(12) United States Patent
Shepherd

(10) Patent No.: US 6,198,102 B1
(45) Date of Patent: Mar. 6, 2001

(54) INSPECTION OF CONTAINER MOUTH USING INFRARED ENERGY EMITTED BY THE CONTAINER BOTTOM

(75) Inventor: William T. Shepherd, Evans City, PA (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 0 days.

(21) Appl. No.: 09/098,492

(22) Filed: Jun. 17, 1998

(51) Int. Cl.$^7$ ................................................ G01N 21/00
(52) U.S. Cl. .................. 250/340; 250/341.1; 250/330; 250/361.1; 250/223 B
(58) Field of Search .............................. 250/340, 341.1, 250/330, 361.1, 223 B

(56) References Cited

U.S. PATENT DOCUMENTS

| | | |
|---|---|---|
| 2,915,638 | 12/1959 | Poole . |
| 3,188,256 | 6/1965 | Shoemaker . |
| 3,356,212 | 12/1967 | Landin . |
| 3,373,869 | 3/1968 | Burson, Jr. . |
| 3,968,368 | 7/1976 | Sager . |
| 4,410,381 | 10/1983 | Chapman, II . |
| 4,915,827 | 4/1990 | Rosenthal . |
| 5,461,228 | 10/1995 | Kirkman et al. . |
| 5,583,337 | * 12/1996 | Chan ...................................... 250/330 |

FOREIGN PATENT DOCUMENTS

| | | |
|---|---|---|
| 4302688 | 8/1994 | (DE) . |
| 0101246 | 2/1984 | (EP) . |
| 0679883 | 11/1995 | (EP) . |

* cited by examiner

Primary Examiner—Constantine Hannaher
Assistant Examiner—Andrew Israel

(57) ABSTRACT

Apparatus for inspecting a container having an open mouth and a closed bottom spaced from the container mouth, while the container is hot from its manufacture, includes a light sensor disposed with respect to the container to view the container bottom through the container mouth. Infrared light energy emitted from the container bottom that travels through the container mouth is directed onto the light sensor, and the inside diameter of the container mouth is measured as a function of the light energy directed onto the sensor. The light sensor preferably comprises an area array sensor for developing a two-dimensional image of the container mouth, and the infrared light energy is directed onto the sensor by a telecentric lens arrangement. The area array sensor is disposed within a camera that has an entrance pupil and the telecentric lens arrangement has one focus at infinity directed toward the container bottom and a second focus at the entrance pupil of the camera. The area array sensor is coupled to image processing electronics for determining or calculating a circle of greatest diameter that will fit into the two-dimensional image of the container mouth, and treating such circle as indicative of the effective inside diameter of the container mouth.

19 Claims, 1 Drawing Sheet

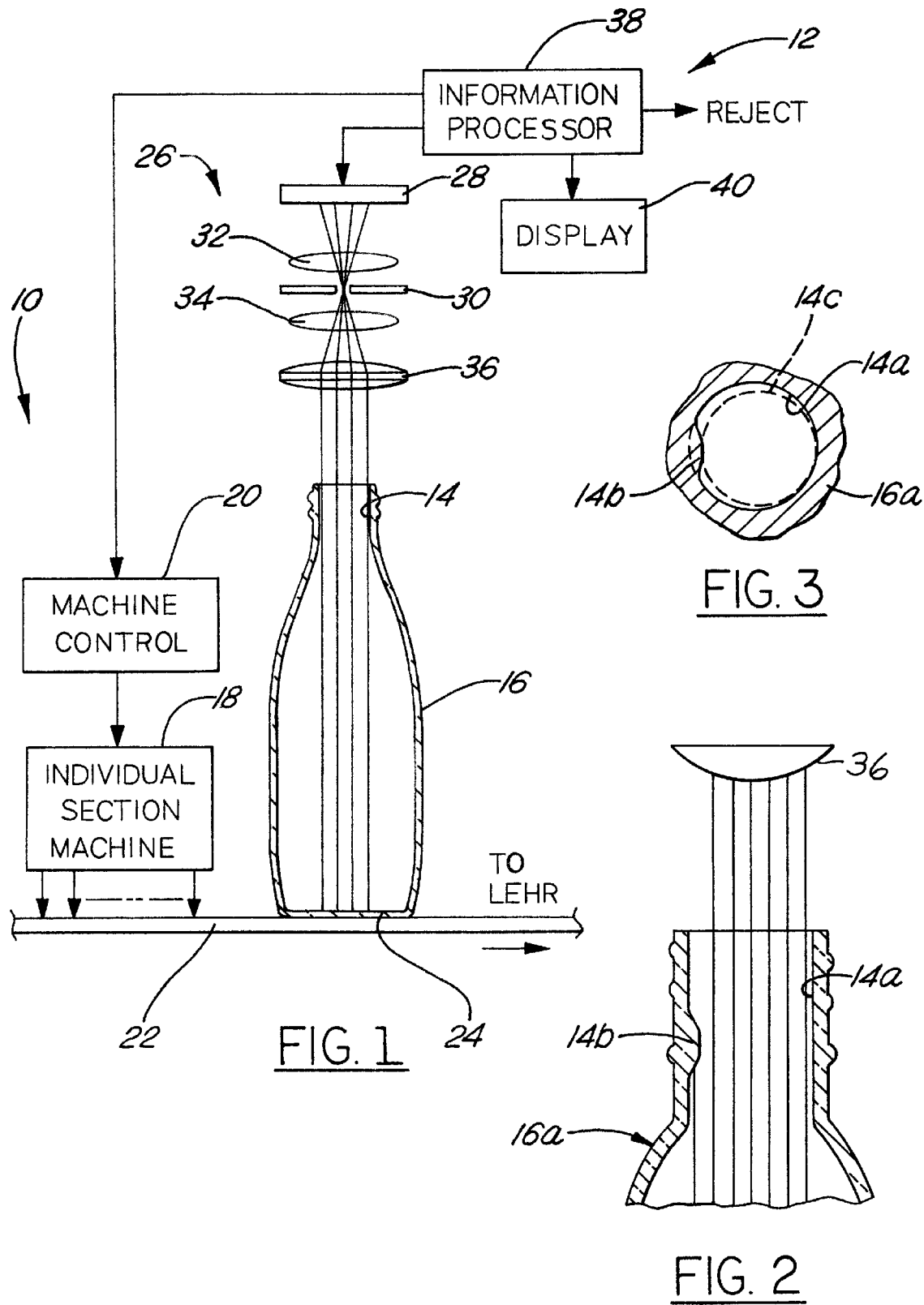

INSPECTION OF CONTAINER MOUTH USING INFRARED ENERGY EMITTED BY THE CONTAINER BOTTOM

The present invention is directed to non-contact measurement of container dimensional parameters, and more particularly to an apparatus and method for measuring inside diameter of a container mouth at the hot end of the container manufacturing process.

BACKGROUND AND OBJECTS OF THE INVENTION

In the manufacture of translucent containers such as clear or colored glass bottles, it is important to maintain dimensional parameters of each container within design specifications for both functional and aesthetic reasons. For example, it is important that the finish of the container, including particularly the container mouth, possess desired geometric characteristics so that the container can be accepted by automatic filling and capping equipment without damage to the equipment, fracture of the container or jamming of the process line.

U.S. Pat. No. 3,313,409, assigned to the assignee hereof, discloses a container inspection system in which containers are routed in sequence through a plurality of inspection stations at which various geometric and other properties are measured. At one such station, an attempt is made to insert a plug of predetermined size into the mouth of the container. The diameter of the plug is coordinated with the minimum container mouth diameter for mating with container filling equipment, for example. If the plug cannot be so inserted into the container mouth, the container is rejected. At other stations of the inspection system, container dimensional parameters are measured by monitoring the positions of rollers in contact with the container as the container is rotated. However, the inspection techniques that require physical contact with the container are slow, and are subject to mechanical wear of the rollers and plugs, for example. The reciprocating motions needed to bring the plugs and rollers into and out of contact with the container draw substantial amounts of electrical power. Furthermore, physical contact of measuring equipment with the container is not desirable at the so-called hot end of the manufacturing process, at which the containers are still soft.

To address some of the deficiencies of the mechanical inspection techniques so described, U.S. Pat. No. 5,461,228, also assigned to the assignee hereof, discloses an apparatus and method for electro-optically measuring dimensional parameters of a container, such as inside diameter of the container mouth. A light source directs light energy into the container, and a light sensor is disposed with respect to the light source and the container to receive light energy transmitted out of the container through the container mouth. A telecentric lens directs onto the light sensor only light energy transmitted through the container mouth substantially axially of the container mouth. The light energy is focused through an iris onto a matrix array sensor, which develops a two-dimensional image of the container mouth. The matrix array sensor is coupled to image processing electronics for determining or calculating a circle of greatest diameter that will fit within the two-dimensional image of the container mouth, and treating such circle as indicative of the effective inside diameter of the container mouth.

In conventional glassware manufacturing processes, glassware is molded in an individual section machine and then placed while still hot on a linear conveyor for transport to an annealing lehr. After stress relief within the lehr, the glassware is transported to various stations for inspection, filling and/or packaging. The lehr divides the hot end of the manufacturing process in which the containers are molded from the cold end of the process in which the containers are inspected and packaged. The techniques for measuring diameter of the container mouth described above are specifically suited for use at the cold end of the manufacturing process. However, it is desirable to implement inspection at the hot end of the manufacturing process so that information on containers having undesirable variations can be obtained quickly and the process corrected. It is therefore a general objective of the present invention to provide a method and apparatus for inspecting containers, particularly for measuring the inside diameter of the container mouth, that can be implemented at the hot end of the manufacturing process. When the containers are directed onto the conveyor following the molding process, the containers are hot, emitting radiation in both the visible and infrared ranges. As the containers travel toward the annealing lehr, they gradually cool, with the rate of cooling depending upon thickness of the individual portions of the container. For example, the container finish and mouth, which are relatively thin, cool more rapidly than the container bottom and heel which are relatively thick. It has heretofore been proposed to measure infrared radiation emitted by a container at the hot end of the manufacturing process to determine or infer wall thickness of different portions of the container. See, for example, U.S. Pat. Nos. 2,915,638 and 3,356,212.

SUMMARY OF THE INVENTION

A method of inspecting containers manufactured in a process from which the containers emerge at elevated temperature, and after which portions of the container cool at different rates as a function of thickness, contemplates in accordance with a presently preferred embodiment of the invention optically viewing a first portion of the container against a background that includes a second portion of the container at higher temperature than the first portion, such that the first portion is effectively illuminated by infrared energy from the second portion of the container. Commercial variations in the second portion of the container, consisting of variations that affect commercial acceptability of the container, are identified in the second portion of the container as a function of variations in the infrared energy caused by the second portion of the container. The first portion of the container is viewed by a light sensor that provides an output as a function of optical characteristics of the first container portion, and commercial variations are detected as a function of such signals.

In a particularly preferred implementation of the invention for inspecting the open mouth of a container, the light sensor is directed to view the bottom of the container through the open container mouth so as to obtain an image of the container mouth as illuminated by infrared energy radiated by the container bottom The infrared energy emerging from the container mouth is directed onto the sensor by a telecentric lens in accordance with the preferred embodiment of the invention, so that only light energy that emerges axially from the container mouth is directed onto the sensor. The sensor is coupled to image processing electronics for determining or calculating a circle of greatest diameter that will fit within the two-dimensional image of the container mouth, and treating such circle as indicative of the effective inside diameter of the container mouth.

Apparatus for inspecting a container having an open mouth and a closed bottom spaced from the container mouth, while the container is hot from its manufacture in accordance with another aspect of the present invention, includes a light sensor disposed with respect to the container to view the container bottom through the container mouth. Infrared light energy emitted from the container bottom that travels through the container mouth is directed onto the light sensor, and the inside diameter of the container mouth is measured as a function of the light energy directed onto the sensor. The light sensor preferably comprises an area array sensor for developing a two-dimensional image of the container mouth, and the infrared light energy is directed onto the sensor by a telecentric lens arrangement. The area array sensor is disposed within a camera that has an entrance pupil, and the telecentric lens arrangement has one focus at infinity directed toward the container bottom and a second focus at the entrance pupil of the camera. The matrix array sensor is coupled to image processing electronics for determining or calculating a circle of greatest diameter that will fit into the two-dimensional image of the container mouth, and treating such circle as indicative of the effective inside diameter of the container mouth.

Thus, in accordance with yet another aspect of the present invention, there are provided a method and apparatus for inspecting for commercial variations in a container, including dimensional characteristics of the container such as inside diameter of the container mouth. The method and apparatus in accordance with this aspect of the invention contemplates directing light energy onto a first portion of the container under inspection, viewing the first portion of the container with a light sensor that provides an output as a function of the optical characteristics of the viewed container portion, and identifying commercial variations in the first portion of a container as a function of such output. In accordance with the invention, the step of illuminating the first portion of the container is accomplished by a second portion of the container at elevated temperature so as to transmit infrared energy onto the first container portion and thereby effectively illuminate the first container portion for inspection.

BRIEF DESCRIPTION OF THE DRAWINGS

The invention, together with additional objects, features and advantages thereof, will be best understood from the following description, the appended claims and the accompanying drawings in which:

FIG. 1 is a schematic diagram of an electro-optical non-contact system for measuring inside diameter of a container mouth in accordance with a presently preferred implementation of the invention;

FIG. 2 is a fragmentary schematic diameter of a portion of FIG. 1 on an enlarged scale; and FIG. 3 is a schematic diagram that illustrates calculation of effective inside diameter from a two-dimensional image of the container mouth.

DETAILED DESCRIPTION OF PREFERRED EMBODIMENTS

FIG. 1 illustrates a glassware manufacturing system 10 that includes apparatus 12 for inspecting or measuring the inside diameter of the mouth 14 of a container 16 at the hot end of the manufacturing process in accordance with a presently preferred embodiment of the invention. Containers 16 are manufactured in a so-called individual section machine 18 under control of machine control electronics 20. Individual section machine 18 may be as disclosed, for example, in U.S. Pat. No. 4,362,544. U.S. Pat. Nos. 4,152, 134 and 4,369,052 illustrate exemplary machine control electronics 20. Containers manufactured by machine 18 are placed on a conveyor 22 for transport in a linear sequence to an annealing lehr. Immediately after manufacture, the containers 16 are hot, emitting radiation in both the visible and infrared regions. As the containers are transported toward the annealing lehr, the containers cool, with different portions of the containers cooling at differing rates depending upon thickness. For example, the finish portion of the container around mouth 14 is relatively thin and cools relatively rapidly, while the bottom 24 of the container is relatively thick and cools more slowly. Closely following machine 18 where the sidewall and mouth of the container are relatively cool, the bottom is typically still bright red, emitting radiation in the infrared range of about 0.4 to 100 microns. In accordance with the present invention, a hot and infrared-emitting portion of the container, such as bottom 24, is used as a light source for illuminating a portion of the container to be inspected, such as mouth 14.

A camera 26 is positioned above conveyor 22 and oriented downwardly for viewing the mouths 14 of containers 16 as they are transported beneath camera 26 in sequence. Camera 26 includes an area array CCD sensor 28, an entrance pupil 30, and lenses 32, 34 associated with the entrance pupil. Sensor 28 is responsive to infrared energy in the range of 0.4 to 1.1 microns. A telecentric lens 36 is positioned between camera 26 and containers 16 as they pass in sequence. Telecentric lens 36 has a first focus in the direction of containers 16 at infinity, and a second focus at entrance pupil 30. That is, camera 26 is positioned with respect to lens 36 so that entrance pupil 30 is spaced from lens 36 by the focal distance of the lens. Thus, pupil 30 with lenses 32, 34 functions as an iris in combination with lens 36 for focusing onto sensor 28 essentially only light rays that emerge from container mouth 14 parallel to the axis of the container, lens and camera. That is, light rays that emerge from the container mouth in a direction not parallel to the container and optical axis, and light rays generated by other portions of the container that may still be hot and emitting infrared radiation, will be directed by lens 36 other than through pupil 30, and thus effectively blocked from impingement on sensor 28. In this way, a clear image of the container mouth is focused onto area array sensor 28. Sensor 28 is connected to information processing electronics 38 for scanning the sensor and developing a two-dimensional image of the container mouth. As illustrated in FIG. 3, the glass that defines the container mouth will appear as a dark image against a bright background formed by the infrared flight energy transmitted from container bottom 24 through the container mouth. This is because the glass of the container reflects or refracts light transmitted onto the body of the container, this reflected or refracted light will not be parallel to the optical axis and thus not directed onto sensor 28. Exemplary techniques for scanning an area array sensor and developing a two-dimensional image of the container mouth are disclosed in U.S. Pat. No. 4,958,223.

FIGS. 2–3 illustrate operation of the invention in connection with a container 16a having a mouth 14a with a choked region 14b. As illustrated in FIG. 2, the choked region 14b blocks a portion of the light rays emerging from the container mouth parallel to the container/optical axis, thereby creating at sensor 28 and information processor 38 a two-dimensional image as illustrated in FIG. 3. Information processor 38 analyzes the image of FIG. 3 by calculating a circle 14c of greatest diameter that will fit within the image of mouth 14a, including choked region 14b. The calculated circle 14c is then treated as the effective inside diameter of the container mouth. In the event that such effective diameter is less than a minimum desired inside diameter, information processor 38 supplies an appropriate signal to a reject mechanism for removing container 16a from conveyor 22. Information processor 38 is also coupled to a display 40 for displaying to an operator the two-dimensional image of the container under inspection, or other appropriate inspection information. Information processor 38 is also coupled to machine control electronics 20 for controlling positioning and operation of operating mechanisms in the individual section machine so as to correct the process variation if possible, or to terminate operation of individual molds or sections at which the container 16a is manufactured. In this connection, it will be appreciated that the containers are placed on conveyor 22 by machine 18 in a predetermined and continuous sequence, so that the section and molds at which a particular container 16 or 16a originated can be readily determined. See, for example, U.S. Pat. No. 4,762,544.

The invention may also be employed for measuring other container parameters and geometric characteristics. For example, a so-called "leaner" container—i.e., a container in which the mouth 14 is cocked with respect to the optical axis of the inspection apparatus, will produce an image of two overlapping circles from opposing edges of the container mouth at the top and bottom of the container neck. If the effective diameter across these overlapping circles is too small, the container would be rejected as having a container mouth diameter less than the desired minimum. The apparatus of the invention may also be employed to detect and reject a container having a so-called "bird swing" variation if the variation is sufficiently large to be viewed across the mouth of the container.

What is claimed is:

1. A method of inspecting containers manufactured in a process from which the containers emerge at elevated temperature, and after which portions of the containers cool at different rates as a function of thickness, said method comprising the steps of:
   (a) optically viewing a first portion of the container against a background that includes a second portion of the container at higher temperature than said first portion, such that said first portion is effectively illuminated by infrared energy emitted by said second portion, and
   (b) identifying commercial variations in the first portion of the container as a function of variations in said infrared energy caused by said first portion of the container.

2. The method set forth in claim 1 wherein said step (a) is carried out by viewing the first container portion with light sensing means that provides an output as a function of optical characteristics of said first portion as illuminated by said second portion, and when said step (b) is carried out as a function of said signals.

3. The method set forth in claim 2 for inspecting a container having an open mouth and a container bottom spaced from said mouth, wherein said step (a) comprises the step of viewing the container bottom through the open mouth to obtain an image of the container mouth as illuminated by infrared energy from the container bottom.

4. The method set forth in claim 3 wherein said light sensor comprises an area array sensor.

5. The method set forth in claim 3 comprising the step of directing the infrared light energy emerging from the container mouth onto said sensor through a telecentric lens in such a way that only light energy that emerges axially from the container mouth is directed onto said sensor.

6. The method set forth in claim 5 wherein said step (b) comprises the steps of:
   (b1) developing a two-dimensional image of the container mouth as a function of light energy directed onto said sensor, and
   (b2) determining a geometric property of the container mouth as function of said two-dimensional image.

7. The method set forth in claim 6 wherein said step (b2) comprises the step of analyzing said two-dimensional image to determine inside diameter of the container mouth.

8. The method set forth in claim 7 wherein said step (b2) is carried out by determining a circle of greatest diameter that will fit within said image and treating said circle as defining the effective inside diameter of the container mouth.

9. The method set forth in claim 3 for inspecting a series of containers having bottoms resting on a moving conveyor and open mouths directed upwardly, wherein said step (a) comprises the step of viewing each container from above as it passes in turn on said conveyor.

10. Apparatus for inspecting a container having an open mouth and a closed bottom spaced from the container mouth while the container is hot from its manufacture, said apparatus comprising:
    a conveyor for supporting the container by means of the container bottom resting on said conveyor with the open mouth of the container directed upwardly, and for transporting the container through an inspection station,
    light sensing means disposed at said station with respect to the conveyor to view the container bottom downwardly through the container mouth while the container bottom is supported on said conveyor,
    means for directing onto said light sensing means infrared light energy emitted by the container bottom that travels upwardly through said mouth, and
    means for measuring inside diameter of the container mouth as a function of the infrared light energy directed onto said light sensing means.

11. The apparatus set forth in claim 10 wherein said light sensing means comprises an array sensor, and wherein said light directing means comprises telecentric lens means for directing into said array sensor only infrared light energy from the container bottom that emerges substantially axially through the container mouth.

12. The apparatus set forth in claim 11 wherein said light sensing means comprises a camera having an entrance pupil, and wherein said telecentric lens means has one focus at infinity directed toward the container bottom and a second focus at said entrance pupil.

13. The apparatus set forth in claim 12 wherein said light sensor comprises an area array sensor and means coupled to said sensor for developing a two-dimensional image of the container mouth.

14. The apparatus set forth in claim 13 wherein said light sensing means further comprises means for analyzing said image to determine inside diameter of the container mouth.

15. The apparatus set forth in claim 14 wherein said analyzing means comprises means for determining a circle of greatest diameter that will fit within said image.

16. The apparatus set forth in claim 15 further comprising means for indicating acceptability of the container as a function of said circle of greatest diameter.

17. The apparatus set forth in claim 10 for inspecting a series of said containers wherein said conveyor is disposed to transport the containers in linear sequence beneath said light sensing means while the container bottoms are supported by said conveyor.

18. A method of inspecting for commercial variations in a first portion of a container that comprises the steps of: (a) directing light energy onto the first container portion under inspection, (b) viewing the first container portion onto which light energy is directed in said step (a) with light sensing means that provides an output as a function of optical characteristics of the viewed container portion, and (c) identifying the commercial variations in the first container portion viewed in said step (b) as a function of said output, characterized in that said step (a) is accomplished by a second portion of the container at elevated temperature that directs infrared light energy onto the first container portion.

19. Apparatus for inspecting a container having an open mouth, which comprises:

a light source for directing light energy into the container, and light sensing means disposed with respect to said light source and the container to receive light energy transmitted through the container mouth, characterized in that said light source comprises a wall portion of the container at a temperature such that said wall portion transmits infrared light energy into the container and to which said light sensing means is responsive.

* * * * *